United States Patent
Lerch et al.

(10) Patent No.: US 8,535,314 B2
(45) Date of Patent: Sep. 17, 2013

(54) SURGICAL CONNECTING ELEMENT FOR FIXING ADJACENTLY ARRANGED BONE PLATES

(75) Inventors: Karl-Dieter Lerch, Witten (DE); Manfred Fischer, Tuttlingen (DE); Klaus-Dieter Steinhilper, Tuttlingen (DE); Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 507 days.

(21) Appl. No.: 11/980,101

(22) Filed: Oct. 30, 2007

(65) Prior Publication Data

US 2008/0172097 A1 Jul. 17, 2008

Related U.S. Application Data

(63) Continuation of application No. 11/150,731, filed on Jun. 10, 2005, now abandoned, which is a continuation of application No. 10/133,260, filed on Apr. 26, 2002, now Pat. No. 6,921,401.

(30) Foreign Application Priority Data

Oct. 30, 1999 (DE) .................................. 199 52 359

(51) Int. Cl.
*A61B 17/66* (2006.01)
*A61B 17/56* (2006.01)
(52) U.S. Cl.
USPC ........................................... 606/71; 606/282
(58) Field of Classification Search
USPC ................ 606/280–310, 74, 70–71, 902–906
See application file for complete search history.

(56) References Cited

U.S. PATENT DOCUMENTS 261,501 A 7/1882 Vandermark
1,724,394 A * 8/1929 Chamberlain ................ 403/281
(Continued)

FOREIGN PATENT DOCUMENTS

DE 912 619 5/1954
DE 2 125 556 7/1971
(Continued)

OTHER PUBLICATIONS

Patent Abstracts of Japan, Abstract of Japanese Patent "Cranio-Knochenschallapen Fixing Device", Publication No. 05220174, Aug. 31, 1993, Japanese Application No. 04056619, Filed Feb. 10, 1992.

(Continued)

*Primary Examiner* — Matthew Lawson
(74) *Attorney, Agent, or Firm* — RatnerPrestia (57) ABSTRACT

In order to configure, in such a way as to be capable of being employed in a simple and secure manner and produced cost-effectively, a surgical connecting element for fixing adjacently arranged bone plates, comprising a first bearing element, a second bearing element and a coupling element, by means of which the first and second bearing element can be coupled to each other in such a way that bone plates lying between the first and second bearing element can be fixed, it is proposed that the second bearing element and the coupling element be so designed and adapted to each other that, by relative movement between the coupling element and the second bearing element transversely to a clamping direction, the bone plates are fixable between the first and the second bearing element.

41 Claims, 6 Drawing Sheets

(56) References Cited

U.S. PATENT DOCUMENTS

| | | | | |
|---|---|---|---|---|
| 2,489,870 A | * | 11/1949 | William | 606/310 |
| 2,576,649 A | * | 11/1951 | Slind | 27/21.1 |
| 2,856,933 A | | 10/1958 | Hildebrand et al. | |
| 3,476,115 A | | 11/1969 | Graeff et al. | |
| 3,831,608 A | | 8/1974 | Kletschka | |
| 3,910,281 A | | 10/1975 | Kletschka et al. | |
| 4,177,813 A | | 12/1979 | Miller et al. | |
| 4,754,529 A | * | 7/1988 | Paradis | 24/16 PB |
| 4,765,329 A | | 8/1988 | Cumming et al. | |
| 4,802,477 A | * | 2/1989 | Gabbay | 606/74 |
| 4,966,600 A | | 10/1990 | Songer et al. | |
| 5,021,059 A | * | 6/1991 | Kensey et al. | 606/213 |
| 5,201,737 A | * | 4/1993 | Leibinger et al. | 606/284 |
| 5,242,459 A | | 9/1993 | Buelna | |
| 5,250,049 A | | 10/1993 | Michael | |
| 5,258,011 A | * | 11/1993 | Drews | 606/220 |
| 5,269,809 A | * | 12/1993 | Hayhurst et al. | 606/232 |
| 5,350,399 A | * | 9/1994 | Erlebacher et al. | 606/213 |
| 5,423,858 A | * | 6/1995 | Bolanos et al. | 606/220 |
| 5,433,727 A | | 7/1995 | Sideris | |
| 5,454,821 A | | 10/1995 | Harm et al. | |
| 5,466,241 A | | 11/1995 | Leroy et al. | |
| 5,527,341 A | * | 6/1996 | Gogolewski et al. | 606/232 |
| 5,549,620 A | | 8/1996 | Bremer | |
| 5,549,621 A | * | 8/1996 | Bessler et al. | 606/151 |
| 5,601,557 A | * | 2/1997 | Hayhurst | 606/232 |
| 5,707,373 A | * | 1/1998 | Sevrain et al. | 606/916 |
| 5,800,436 A | * | 9/1998 | Lerch | 606/324 |
| 5,814,071 A | | 9/1998 | McDevitt et al. | |
| 5,868,746 A | | 2/1999 | Sarver et al. | |
| 5,893,850 A | | 4/1999 | Cachia | |
| 5,919,205 A | | 7/1999 | Heimberger et al. | |
| 5,921,896 A | | 7/1999 | Bonutti | |
| 5,921,986 A | * | 7/1999 | Bonutti | 606/60 |
| 6,022,351 A | * | 2/2000 | Bremer et al. | 606/324 |
| 6,063,106 A | | 5/2000 | Gibson | |
| 6,093,201 A | * | 7/2000 | Cooper et al. | 606/232 |
| 6,096,058 A | | 8/2000 | Boche | |
| 6,190,389 B1 | * | 2/2001 | Wellisz et al. | 606/86 B |
| 6,258,091 B1 | | 7/2001 | Sevrain et al. | |
| 6,270,500 B1 | | 8/2001 | Lerch | |
| 6,328,743 B2 | | 12/2001 | Lerch | |
| 6,355,044 B1 | * | 3/2002 | Hair | 606/326 |
| 6,379,363 B1 | * | 4/2002 | Herrington et al. | 606/79 |
| 6,485,493 B1 | * | 11/2002 | Bremer | 606/70 |
| 6,585,739 B2 | * | 7/2003 | Kuras et al. | 606/301 |
| 6,589,244 B1 | * | 7/2003 | Sevrain et al. | 606/916 |
| 6,685,707 B2 | | 2/2004 | Roman et al. | |
| 6,755,834 B2 | | 6/2004 | Amis | |
| 2002/0156475 A1 | | 10/2002 | Lerch et al. | |
| 2004/0210224 A1 | | 10/2004 | Ahmad et al. | |
| 2006/0009772 A1 | * | 1/2006 | Lerch | 606/72 |

FOREIGN PATENT DOCUMENTS

| | | |
|---|---|---|
| DE | 28 04 070 | 1/1978 |
| DE | 78 02 791 | 5/1978 |
| DE | 37 09 067 | 9/1988 |
| DE | 89 10 462 | 4/1990 |
| DE | 691 08 236 | 11/1991 |
| DE | 42 43 427 | 12/1992 |
| DE | 296 14 921 U | 10/1996 |
| DE | 694 06 972 | 11/1997 |
| DE | 299 19 090 | 1/2000 |
| DE | 198 32 797 | 2/2000 |
| EP | 0 602 757 | 6/1994 |
| EP | 0 628 286 | 12/1994 |
| EP | 0 787 466 | 8/1997 |
| WO | WO00/49949 | 8/2000 |

OTHER PUBLICATIONS

European Search Report, EP 05 01 9175, Completed Jul. 17, 2006.

* cited by examiner

SURGICAL CONNECTING ELEMENT FOR FIXING ADJACENTLY ARRANGED BONE PLATES

CROSS-REFERENCE TO RELATED APPLICATIONS

This application is a continuation application of application Ser. No. 11/150,731, filed Jun. 10, 2005, now abandoned, which is a continuation of application Ser. No. 10/133,260, filed Apr. 26, 2002, now U.S. Pat. No. 6,921,401, which is a continuation of International Application No. PCT/EP00/10547, filed Oct. 26, 2000, which claims the benefit of priority of German Application No. 199 52 359.2, filed Oct. 30, 1999. The contents of the foregoing applications are incorporated herein by reference in their entirety and for all purposes.

BACKGROUND OF THE INVENTION

The invention relates to a surgical connecting element for fixing adjacently arranged bone plates, comprising a first bearing element, a second bearing element and a coupling element for coupling the first and second bearing element to each other in such a way that bone plates lying between the first and second bearing element are fixable.

In order to allow the surgeon access to the region on which the operation is to be performed, the patient's skullcap, for example in the case of craniosurgical interventions, is opened by removing a skullcap segment from the skullcap by means of craniotomy incisions with an incision gap being formed, in order thus to obtain access to the underlying brain. After the operation, the skullcap segment removed from the skullcap must be fitted into the skullcap again and fixed to the remaining skullcap.

DE 296 14 921 U1 discloses a surgical connecting element for fixing a skullcap segment removed from a skullcap to the remaining skullcap, in which the connecting element comprises a connecting shank which can be introduced into an incision gap between skullcap segment and remaining skullcap, a connecting head for overlapping the incision gap, and a bearing element which projects laterally from the connecting shank and can be laid against the skullcap segment and the remaining skullcap.

EP 0 787 466 discloses a device for fixing a piece of bone cut out of the skullcap, for the purpose of an operative intervention, in an exposed region on the remaining skull bone, in the case of which a centrally apertured disc as first and second bearing element can be pushed onto a shank as coupling element and one disc has cuts extending radially outwards. A tool is used to fix the disc to the shank. A threaded connection may also be employed.

U.S. Pat. No. 4,802,477 discloses a device for securing a sternum in a closed position after opening. A corresponding fixing collar engages in a threaded rod.

The object of the invention is to design a surgical connecting element of the generic type in such a way that it can be employed in a simple and secure manner and produced cost-effectively, and in particular biocompatible and resorbable materials can be used.

SUMMARY OF THE INVENTION

This object is achieved in the case of a surgical connecting element of the type described at the outset in that the second bearing element and the coupling element are so designed and adapted to each other that, by relative movement between the coupling element and the second bearing element transversely to a clamping direction, the bone plates are fixable between the first and the second bearing element.

As a result of such a configuration, it is no longer necessary to provide a threaded connection or clamped connection over the entire circumference of a shank, but rather the coupling between the second bearing element and the coupling element can be produced in a simple and yet secure manner. As a result, there is a greater choice of materials which can be employed to produce the surgical connecting element, since it is no longer necessary to cut a thread.

In the case of thread cutting or else clamping over the entire circumference, preference is given to the use of metals to obtain good fixing. As a result of the coupling according to the invention, which eliminates the need to provide in particular for thread cutting, it is then also possible to employ for example softer plastics materials, which exhibit high biocompatibility or resorbability and with which a good and secure connection can be produced by the fixing and coupling mechanism according to the invention.

As a result of the configuration according to the invention, it is possible in particular to produce a frictional connection between the second bearing element and the coupling element.

It is particularly advantageous if a fixing position of the first and of the second bearing element can be locked by relative movement between the coupling element and the second bearing element transversely to the clamping direction. As a result, secure fixing can be achieved in a simple way with connecting elements which can be produced cost-effectively.

For the same reason, it is particularly favorable if a fixing position of the first and of the second bearing element can be unlocked by relative movement between the coupling element and the second bearing element transversely to the clamping direction. It is then possible, for example, to carry out a readjustment in a simple way during an operation.

In order to improve the clamping of bone plates clamped between the first and the second bearing element, it is particularly favorable if the first and/or second bearing element have/has a holding body which can be inserted into an intermediate space between adjacently arranged bone plates. Such a holding body serves as additional wedging and in particular also brings about additional fixing in a direction transverse to the clamping direction.

It is very particularly advantageous if a holding body is designed to be elastic and in particular resilient in the direction transverse to the clamping direction.

As a result, the distance between the bone plates which bear against the holding body can be varied within certain limits in this transverse direction and in particular, when a plurality of connecting elements are used, bracing of a bone plate in relation to surrounding bone plates in the transverse direction can be achieved.

Since the connecting elements remain in the body, it is advantageous if such a connecting element is produced from a biocompatible material. It is very particularly advantageous if the connecting element is fabricated from a resorbable plastics material. Incision gaps between the bone plates knit together again after the operation and, with resorbable material, tissue can also grow over the connecting element, so that the latter is not a "disruptive factor" in the body.

In an advantageous variant of one embodiment, the coupling element is provided with a predetermined breaking point. As a result, the coupling element can be correspondingly shortened in a simple way, in particular once fixing has been effected. It is very particularly advantageous in this case if the predetermined breaking point is so arranged on the coupling element and so designed that breaking can be produced essentially with a tensile stress which brings about optimum biasing of the bone plates. As a result, the fixing can be achieved in a simple way by the surgeon.

Favorably, the first and/or second bearing element have/has a raised edge region for producing a tensile stress in the clamping direction. Such a raised edge region can be deformed during production of the fixing, when bone plates are clamped between the first and the second bearing element. As a result, in the fixing position (clamping position), a force is exerted by the deformed raised edge region which improves the clamping and hence brings about a high degree of fixing security.

It is cost-effective if the first and the second bearing element are of substantially the same construction, since the production is thereby simplified.

Favorably, in this case, the first bearing element can be coupled to the coupling element in a functionally identical manner to the second bearing element.

In a variant of one embodiment, it is provided that the first bearing element is integrally or positively connected to the coupling element. The first bearing element then no longer has to be connected to the coupling element prior to use of a connecting element.

Advantageously, the second bearing element has at least one through-opening for the coupling element, so that the second bearing element and the coupling element are movable relative to each other parallel to the clamping direction.

It is favorable and, in particular from the point of view of fabrication, advantageous in this case if the second bearing element has at least one fixing recess, by means of which the second bearing element and the coupling element can be fixed relative to each other.

In a variant of one embodiment, it is provided that a fixing recess has an extent in a transverse direction, so that the fixing recess is not of radially symmetrical design. This makes possible a coupling which can be produced in a simple way.

Furthermore, it is favorable in particular from the point of view of fabrication, if the second bearing element has at least one through-opening for the coupling element, so that the coupling element and the second bearing element are displaceable relative to each other, and has at least one fixing recess, the at least one through-opening and the at least one fixing recess being interconnected.

In one embodiment, it is provided that the second bearing element can be connected to the coupling element by a relative movement of the entire bearing element with respect to said coupling element.

In a further embodiment, it is provided that bone plates seated between the first and the second bearing element can be fixed by a relative movement of the coupling element with respect to the second bearing element.

Finally, in a further embodiment, it is provided that the second bearing element can be connected to the coupling element by a relative movement of a holding element, seated on the second bearing element, with respect to the coupling element.

In a variant of one embodiment, it is provided that the coupling element is a rigid body. This means that the coupling element has a defined shape. The coupling element may, however, furthermore have elastic properties, that is be capable for example of elastic deformation.

Favorably, the coupling element is so dimensioned that, in a direction transverse to its longitudinal direction, it has a greater width than in the transverse direction perpendicular thereto. As a result, the coupling element is of strip-shaped design. On positioning the connecting element, the longer side lies in an incision gap and the distance between adjacent bone plates is (when bearing against the coupling element) essentially defined by the width of the narrower side. As a result, on the one hand the width of the bone gap is reduced and on the other hand a secure coupling between the second bearing element and the coupling element can be achieved, without the need to provide for example a thread on the coupling part and second bearing element.

In a variant of one embodiment, provision is made for the coupling element to be of substantially rotationally symmetrical design in its longitudinal direction.

Such an embodiment is advantageous for example when bone plates which are to be fixed with respect to one another have a shape which deviates greatly from a flat shape and connecting elements have to be set in place accordingly. If the coupling element then has a certain flexibility in particular in the radial direction, better fixing can be achieved in such cases.

It is very particularly advantageous if the coupling element has at least one fixing opening, in which a corresponding holding element, for example a holding tongue in particular in the form of a spring tongue, of the second bearing element can engage.

With a substantially rotationally symmetrical design of the coupling element in the longitudinal direction, a fixing recess favorably runs around the circumference of the coupling element. As a result, the latter can be variably employed.

In a variant of one embodiment, it is provided that adjacent fixing recesses are separated by a disc-shaped element. As a result of such disc-shaped elements, flat holding surfaces are made available, against which the second bearing element can bear in order to fix it in this way.

In another variant of one embodiment, it is provided that adjacent fixing recesses are separated by a spherical element. By such a spherical element a certain variability with respect to the bearing surface is achieved, so that, if necessary, the second bearing element can also be pushed on at an angle to the coupling element, insofar as the geometrical circumstances relating to the fixing of the bone flap require this.

Favorably, the holding element of the second bearing element engages in a fixing opening transversely to the clamping direction.

It is very particularly favorable if the coupling element comprises a plurality of fixing openings which are arranged in the longitudinal direction of the coupling element. As a result, appropriate distances can be set between the first and the second bearing element, and in particular the distance required to achieve a good clamping action can be set.

Favorably, in this case, adjacent fixing openings are arranged equidistantly from each other.

It may be provided in particular that the coupling element is provided with an engaging strip formed from fixing openings. The latter is advantageously designed as a latching strip in order thus to enable coupling and fixing in a simple way.

In a variant of one embodiment, it is provided that the coupling element has at least two engaging strips. Favorably, in this case, at least two engaging strips are arranged offset from one another with respect to the distance of fixing openings relative to the first bearing element. As a result of the offset, a finer step subdivision can be achieved without a fixing opening and a web lying between fixing openings themselves having to be made narrower.

In a variant of one embodiment, a lateral surface of the coupling element is provided with an engaging strip. As a result, the engaging strip itself does not abut against the bone plates.

In another variant of one embodiment, an engaging strip is arranged on the coupling element between lateral surfaces of the coupling element. The engagement strip can thereby be arranged over a greater surface area and, accordingly, the coupling improved. For example, with an arrangement on the lateral surface, it is very advantageous if opposite lateral surfaces are each provided with an engaging strip, in order to improve the coupling by increasing the coupling area. With an arrangement between the lateral surfaces, one engaging strip is sufficient, since a greater engaging area can be made available.

It may be provided that an engaging strip is of stepped design. In a further variant, it may be provided that an engaging strip is of sawtooth design. From the point of view of fabrication, it is particularly favorable if an engaging strip comprises rectangular openings as fixing openings.

In an advantageous variant of one embodiment, a fixing opening has a tapering cross-section. With corresponding adaptation of the second bearing element (i.e. corresponding adaptation of a holding part thereof), it is possible to achieve a wedge action for better fixing.

It is favorable if the second bearing element has a holding tongue which can enter into a fixing opening and by means of which the second bearing element can be connected to the coupling element.

In a variant of one embodiment, a holding tongue has a plurality of holding teeth for simultaneous engagement in a plurality of fixing recesses. As a result, increased fixing security is achieved.

It may also be provided that a holding tongue is arranged at an angle to a bearing surface of the second bearing element. As a result, for example a fixing opening can be designed as a through-aperture of rectangular cross-section and good fixing can be achieved by the sloping arrangement of the holding tongue.

It may also be provided that the second bearing element has further holding means for fixing to the coupling element. The further holding means serve for coupling in addition to the holding tongue. In a variant of one embodiment, the second bearing element comprises fixing tongues, between which the holding tongue is arranged and by which the coupling element can be fixed.

For example, the fixing tongues c n embrace the coupling element and thus additionally secure it. It is favorable if the fixing tongues are designed as snap-action tongues, so that as the second bearing element is pushed on a force has to be overcome and one it has been overcome the fixing tongues snap back and thus additionally h ld the second bearing element in a clamping manner.

In one embodiment, it is provided that the second bearing element can be connected to the coupling element by rotation relative to the latter. Favorably, in this case, the second bearing element has a holding tongue which can engage in a fixing recess of the coupling element by rotation of the second bearing element relative to the coupling element.

In a further variant, it is provided that the second bearing element has an introducing slot which is open towards the edge of the second bearing element. Such an embodiment is particularly advantageous if the coupling element is designed in the manner of a shank.

It may be provided in this case that lateral surfaces of the insertion or introducing slot are offset transversely to a bearing surface of the second bearing element. As a result, additional clamping can be achieved, and in particular the lateral surfaces can be provided with opposite teeth which ensure additional interlocking for further securing.

In one embodiment, it is provided that the coupling element is of linearly flexible design. This means that, with reference to a line element, the coupling element is radially isotropically flexible. For example, the coupling element is then formed by a thread or wire. As a result of a coupling element designed in this way, in particular a distance between the first and second bearing element can be adjusted in an infinitely variable manner.

It is favorable if the first bearing element has spaced-apart openings for threading through the linearly flexible coupling element. It is then possible to form a loop between the two openings with respectively drawn-through thread ends, and by pulling on the two thread ends the first bearing element can be put under tensile stress by way of the loop, and thus for example pulled towards a bone plate.

Furthermore, it is advantageous if the second bearing element has at least one opening for feeding through the flexible coupling element. As a result, the fixing, which comprises a fixing of the first and of the second bearing element relative to each other, is facilitated.

In a first variant of one embodiment, the first and the second bearing element can be fixed with bone plates lying therebetween by a knot in the linearly flexible coupling element. With an appropriate choice of knot, it is possible to exert a tensile stress which moves the first and the second bearing element towards each other and fixes bone plates lying therebetween with respect to each other. The knot itself then fixes this fixing position.

In a second variant of one embodiment, it is provided that the second bearing element has a peg element for fixing the linearly flexible coupling element by looping it around. A linearly flexible coupling element, for example a thread or a wire, can be looped or wound around the peg element in a simple way and is thus held on the peg element essentially by frictional force. As a result, a distance between the two bearing elements can be fixed. With an appropriate choice of winding loops, it is further possible to exert a tensile stress which moves the first and the second bearing element towards each other and through further windings a fixing position can then be secured. In addition, a knot may then further be provided once the winding has been effected.

Favorably, in this case, the peg element is arranged in a recess, so that it projects above an outer surface of the second bearing element only a little or not at all, i.e. does not substantially increase the external dimensions of the latter.

It is very particularly advantageous if a fixing recess of the second bearing element comprises a clamping s at for the linearly flexible coupling element. By introducing for example a thread into this clamping seat, the thread is secured, i.e. fixed in relation to he second bearing element. In this way, a distance between the first and the second bearing element can then be fixed and hence bone plates lying alongside each other can also be fixed with respect to each other.

Favorably, in this case, a clamping seat is arranged at a radial distance with respect to a projection of a feed through opening of the first bearing element onto the second bearing element. As a result, an improved clamping action can be achieved, since on introducing the linearly flexible coupling element into a clamping seat by moving transversely to the clamping direction, it is not reduced.

A connecting element according to the invention can be employed in a simple way and produced cost-effective y if the second bearing element can be frictionally fixed to the coupling element.

It is very particularly advantage us if that the relative movement between the second bearing element and the coupling element for the fixing of the second bearing element to the coupling element proceeds from an unfixed position to a fixing position, since locking ca thereby be produced and undone again in a simple way.

The object mentioned at the out et is also achieved, in the case of a surgical connecting element of the type d scribed at the outset, in that the coupling element has at least one fixing recess, in which a corresponding coupling element of the second bearing element can engage for coupling this second bearing element to the coupling element.

Such a surgical connecting element has the same advantages as have already been mentioned above.

Advantageously, in this case, the engagement takes place substantially transversely to a clamping direction. In particular, the second bearing element can be frictionally fixed to the coupling element.

The following description of preferred embodiments of the invention serves to provide a more detailed explanation in conjunction with the drawing.

DETAILED DESCRIPTION OF THE INVENTION

Figure 1:
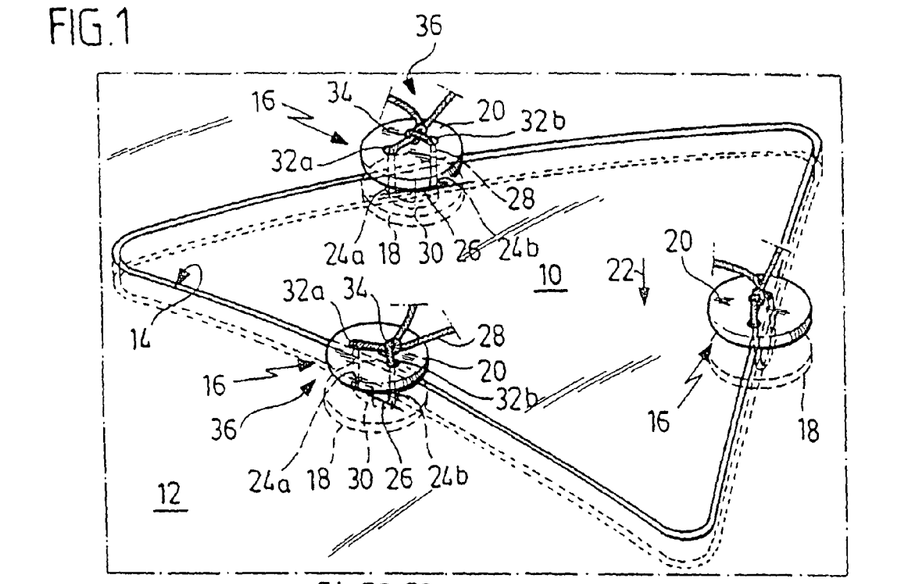
FIG. 1 shows a perspective view of a skullcap segment which has been removed from a skullcap and re-inserted into the remaining skullcap, with bone plates which lie alongside one another being fixed with the aid of connecting elements according to a first embodiment.

An example of the application of a connecting element according to the invention is the fixing of a skullcap segment 10, as shown in FIG. 1, to a surrounding remaining skullcap 12. The skullcap segment 10 has been removed by craniotomy incisions which have formed an incision gap 14 to allow a surgeon access to the brain lying below the skullcap segment 10. When the operation is completed, this skullcap segment 10 is re-inserted. With the aid of connecting elements 16 according to the invention, for example by means of three such connecting elements 16, as illustrated in FIG. 1, the adjacent bone plates 10 and 12 are fixed, so that the skullcap segment 10 can knit to the skullcap 12 again. To this end, such a connecting element 16 is fabricated from a biocompatible material and in particular from a resorbable material, so that body tissue can knit to the connecting element.

In a first embodiment of a connecting element according to the invention, which is shown in FIG. 1, such a connecting element 16 comprises a first disc-shaped bearing element 18 and a second bearing element 20, which is basically of the same construction as the first bearing element. The first bearing element 18 is placed under the skullcap segment 10 and the skullcap 12 and the second bearing element 20 is placed at a distance from it above the skullcap segment 10 and the skullcap 12. By fixing the first bearing element 18 relative to the second bearing element 20 and exerting a clamping force in a clamping direction 22 which, in the exemplary embodiment shown, is substantially perpendicular to the bone plates 10 and 12, the adjacent skullcap segment 10 and the skullcap 12 can be fixed with respect to each other.

The first bearing element 18 has two feed-through openings 24a, 24b which are spaced apart and the connecting line 26 of which preferably lie on a diametral line. A thread or wire 28 as coupling element, which is linearly flexible in the sense that, with reference to a tangential direction vector, there is no preferred direction perpendicular to this direction vector with regard to flexibility, is passed through the spaced feed-through openings 24a and 24b in the first bearing element 18 so as to form between the two feed-through openings 24a and 24b a loop 30 facing into the interior of the skull.

The coupling element 28 is then fed through the incision gap 14 away from the interior of the skull through corresponding openings 32a, b in the second bearing element 20. If a tensile force is exerted outwardly (counter to the clamping direction 22) on corresponding ends of the coupling element 28, this has the effect that the loop 30 bears against the first bearing element 18.

In the exemplary embodiment shown in FIG. 1, the first bearing element 18 and the second bearing element 20 are fixed with respect to each other by way of a knot 34. For this purpose, corresponding ends of the coupling element 28, after they have been passed through the openings 32a and 32b of the second bearing element and the coupling element has been pulled tight, are directed transversely to the clamping direction 22 and knotted together while exerting a tensile stress in order to exert a clamping force by virtue of the fact that the second bearing element 20 is pulled upwards and clamped against the skullcap segment 10 and the skullcap 12 by way of the loop 30. This fixing position or clamping position is secured by the knot 34, i.e. the fixing position 36 is locked.

Thus, by way of the clamping action of the first bearing element 18 and the second bearing element 20 on the bone plates lying in between, the skullcap segment 10 and the skullcap 12 are then fixed relative to each other at least in the region around a connecting element. By using a plurality of such connecting elements 16, the whole of the skullcap segment 10 can then be fixed in relation to the remaining skullcap 12.

Figures 2, 3:
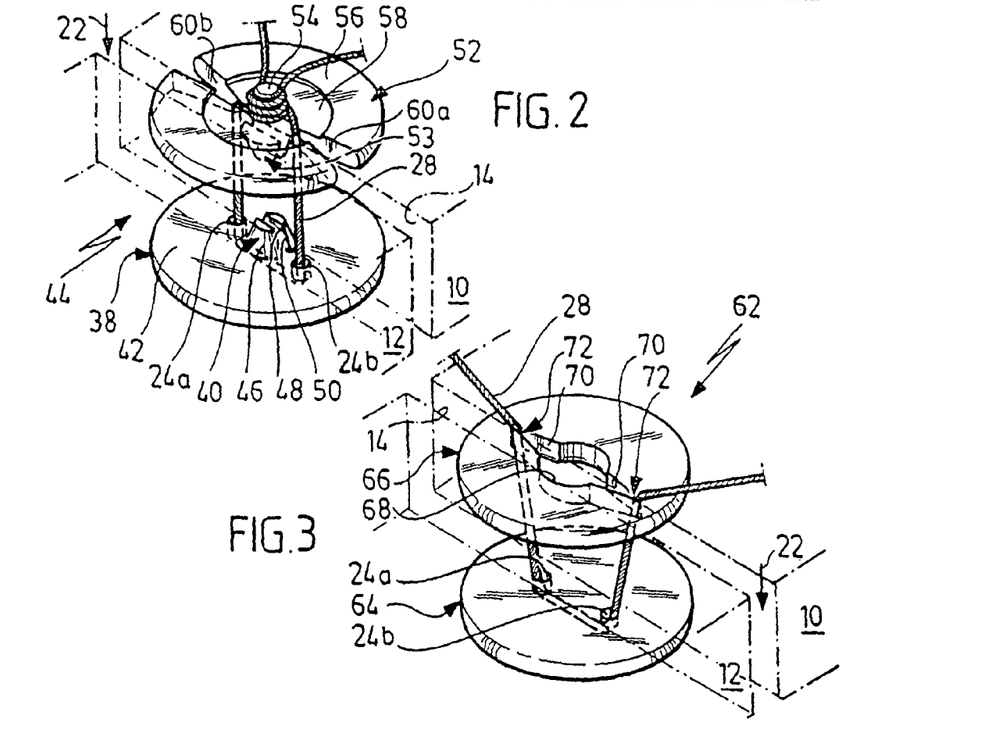
FIG. 2 shows a perspective view of a second embodiment of a connecting element according to the invention with fixed bone plates.
FIG. 3 shows a perspective view of a third embodiment of a connecting element with fixed bone plates.

In a further exemplary embodiment, which is shown in FIG. 2, the first bearing element 38 is basically of the same construction as described for the first exemplary embodiment. However, the first bearing element has, preferably centrally arranged, a holding body 40 which rises above a bearing surface 42. The first bearing element 38, in this second embodiment 44 of a connecting element, is positioned with the holding body 40 in the incision gap 14 between the adjacently arranged bone plates 10 and 12, in order to effect additional wedging and hence better fixing between the two bone plates 10 and 12.

Preferably, the holding body 40 is designed to be elastic and in particular resilient, so that a certain variability in the movement of the two bone plates 10 and 12 towards or away from each other exists, in order to achieve an optimum fixing result.

In the exemplary embodiment shown in FIG. 2, the holding body 40 comprises two opposite pin parts 46 and 48, between which an intermediate space 50 is formed. The pin parts 46 and 48 are in this case designed outwardly frustoconical. The intermediate space 50 defines essentially how far the bone plates can be pushed towards each other in the incision gap; when the two pin parts 46 and 48 abut against each other, the minimum distance between the bone plates is reached.

In the second embodiment 44, there is arranged, in the center of the second bearing element 52, a peg element 54 which is seated in particular in a recess 58 formed in relation to an outer top surface 56, in order that this peg element 54 projects only slightly above the top surface 56 or not at all.

Formed in the second bearing element 52 in the radial direction are laterally open wedge-shaped clearances or cutouts 60a, 60b, through which the flexible coupling element 28 can be fed, in order to be able to loop it, and in particular wind it, around the peg element 24.

The clamping force between the first bearing element 38 and the second bearing element 52 is basically produced as already described above for the first exemplary embodiment. The fixing position is in this case locked, i.e. fixed, by the respective ends of the linearly flexible coupling element 28 being wound around the peg element 54 so that the two positioning elements 38 and 52 are held with respect to each other with the bone plates 10 and 12 lying therebetween. The recesses 60a and 60b serve in this case as feed-in slots for a filamentary coupling element 28.

The second bearing element 52 may in this case likewise have a centrally arranged holding body 53, which is in particular of the same design as the holding body 40 of the first bearing element.

In a third embodiment of a connecting element 62, which is shown in FIG. 3, the first bearing element 64 is designed like the first bearing element 18 according to the first exemplary embodiment (FIG. 1). The second bearing element 66 has a central aperture 68 as feed-through opening for the linearly flexible coupling element 28 for feeding the latter through. Emerging from this central aperture 68 there are formed, oppositely in the radial direction, wedge-shaped cutouts 70. Formed at the radially outer end of such a cutout 70 is a clamping seat 72 as a fixing recess into which the flexible coupling element 28 can be clamped, in order to fix the latter in relation to the second bearing element 66.

A clamping seat 72 is in this case preferably located further to the outside in the radial direction, with reference to a projection of a respective feed-through opening 24a and 24b of the first bearing element 64 in the clamping direction onto the second bearing element 66 (with appropriate alignment of first bearing element 64 and second bearing element 66). As a result, by pulling transversely to the clamping direction 22, bone plates can be clamped between the first bearing element 64 and the second bearing element, it being possible to fix a fixing position by means of the clamping seat 72.

Figure 4:
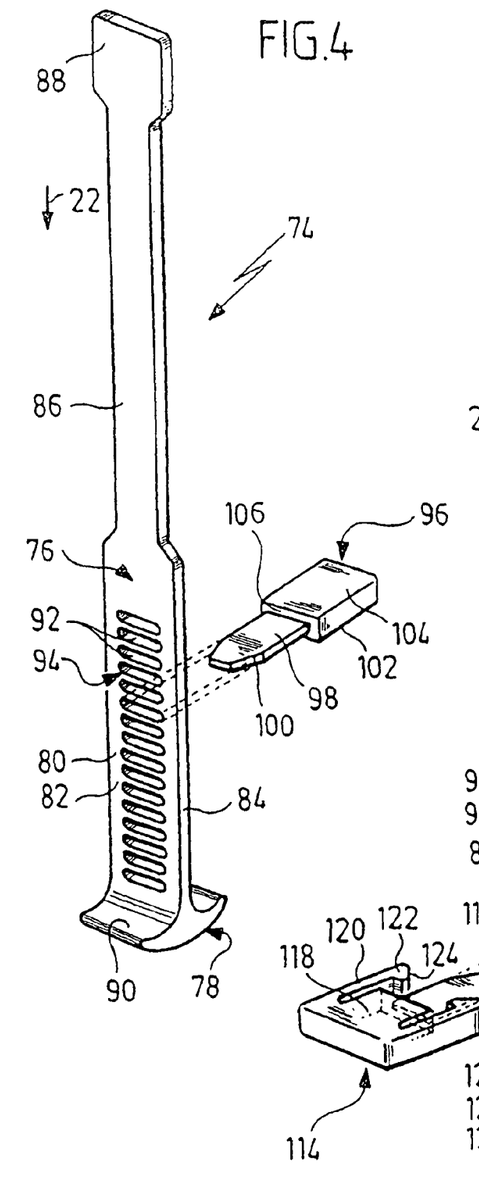
FIG. 4 shows a perspective view of a fourth embodiment of a connecting element according to the invention.

In a fourth embodiment, which is shown in FIG. 4, a connecting element 74 according to the invention comprises a coupling element 76, on which a first bearing element 78 is integrally formed. The coupling element 76 with the first bearing element 78 is in this case rigid in the sense that it has a permanent shape.

The coupling element 76 has a lower region 80 of rectangular cross-section, one side of the rectangle being longer than another, so that the lower region 80 is of strip-shaped configuration. The first bearing element 78 is in this case transverse to the longer side 82 of the lower region 80, so that the narrower side 84 defines the minimum distance between adjacent bone plates on fixing.

Adjoining the lower region 80 is a middle region 86, which is followed by an upper region 88. The middle region 86 has a smaller cross-section with respect to the longer side 82 than the lower region 80 and the upper region 88, so that in particular as a result of the transition between the middle region 86 and the upper region 88 a gripping element is formed, with the aid of which the coupling element 76 can be held or, if necessary, a tensile stress can be exerted on the first bearing element 78 by its bearing surfaces 90.

The middle region 86 is provided with slot-like through-openings 92 which are provided parallel to the bearing surfaces 90 of the first bearing element 78 and are themselves arranged at a uniform distance from one another, so that an engaging strip 94 is formed by the openings 92. As a result, a second bearing element 96 can be frictionally connected to the coupling element 76 at different heights with respect to the first bearing element 78.

The second bearing element 96 has a holding tongue 98 which is adapted to an opening 92 and by means of which the second bearing element 96 is pushed into an opening 92 transversely to the clamping direction 22. The holding tongue 98, of flat design, is for this purpose provided with bevelled edges 100 at its front end, in order to facilitate insertion into an opening 92.

The holding tongue 98 of the second bearing element 96 is seated on an element 104 forming a bearing surface 102 for a bone plate. The holding tongue 98 is in this case seated at a front face of the element 104 in such a way that a transverse bearing surface 106 is formed for the coupling element 76, by means of which transverse bearing surface a pushed-in second bearing element can be supported on the coupling element 76 transversely to the clamping direction 22, which corresponds to the longitudinal direction of the coupling element 76.

The connecting element 74 is positioned with the bearing surfaces 90 under bone plates to be fixed, the lower region 80 of the coupling element 76 then being situated in the incision gap 14. To fix and simultaneously exert a clamping force, the second bearing element 96 is pushed into the corresponding opening 92 transversely to the clamping direction 22. The second bearing element 96 is then frictionally fixed in the opening 92. The holding tongue 98 is designed in this case in particular with such elasticity that it can bend in the clamping direction 22 and accordingly a pushed-in second bearing element 96 exerts a clamping force in the direction of the first bearing element 78.

Figure 5:
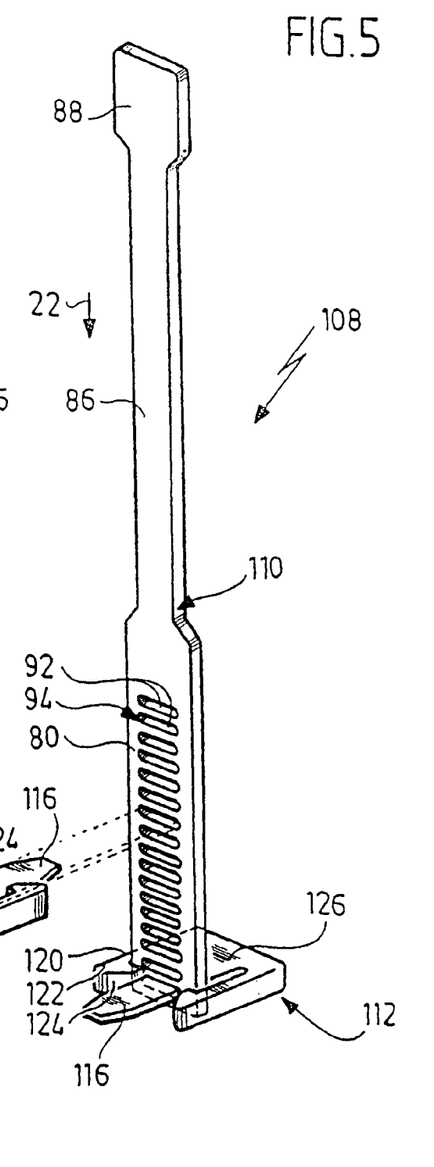
FIG. 5 shows a perspective view of a fifth embodiment of a connecting element according to the invention.

In a fifth embodiment of a connecting element 108, which is shown in FIG. 5, the coupling element 110 is basically of the same construction as in the fourth embodiment just described. However, a first bearing element 112 is not integrally formed with the coupling element 110, but as a separate element which is of substantially the same construction as a second bearing element 114. The second bearing element 114 again comprises a holding tongue 116 for pushing into a corresponding opening 92. The holding tongue 116 is seated on an element 118, on which fixing tongues 120 in the form of holding claws are seated on each side. As the second bearing element 114 is pushed into an opening 92 of the coupling element 110, these fixing tongues 120 embrace the coupling element 110, in order to bring about an additional connection thereto and thus improve the fixing overall. For this purpose, a fixing tongue 120 has at one end a holding tooth 122, having a bevelled edge 124 at its front end to enable the holding tooth to slide over the coupling element 110. The fixing tongue 120 is arranged, for this purpose, on the element 118 in such a way as to be movable transversely to the pushing-in direction. When the second bearing element has been pushed in, the coupling element 110 is seated between the element 118 and the holding teeth 122.

The first bearing element 112, which is of the same configuration as the second bearing element, is pushed in at a lower end of the coupling element 110 and fixed to the coupling element 110 in a manner corresponding to that described above for the second holding element.

Preferably, a bearing surface 126 of the first and second bearing element 112 and 114, respectively, is flat in order to enable a good contact.

Figures 6, 7, 8:
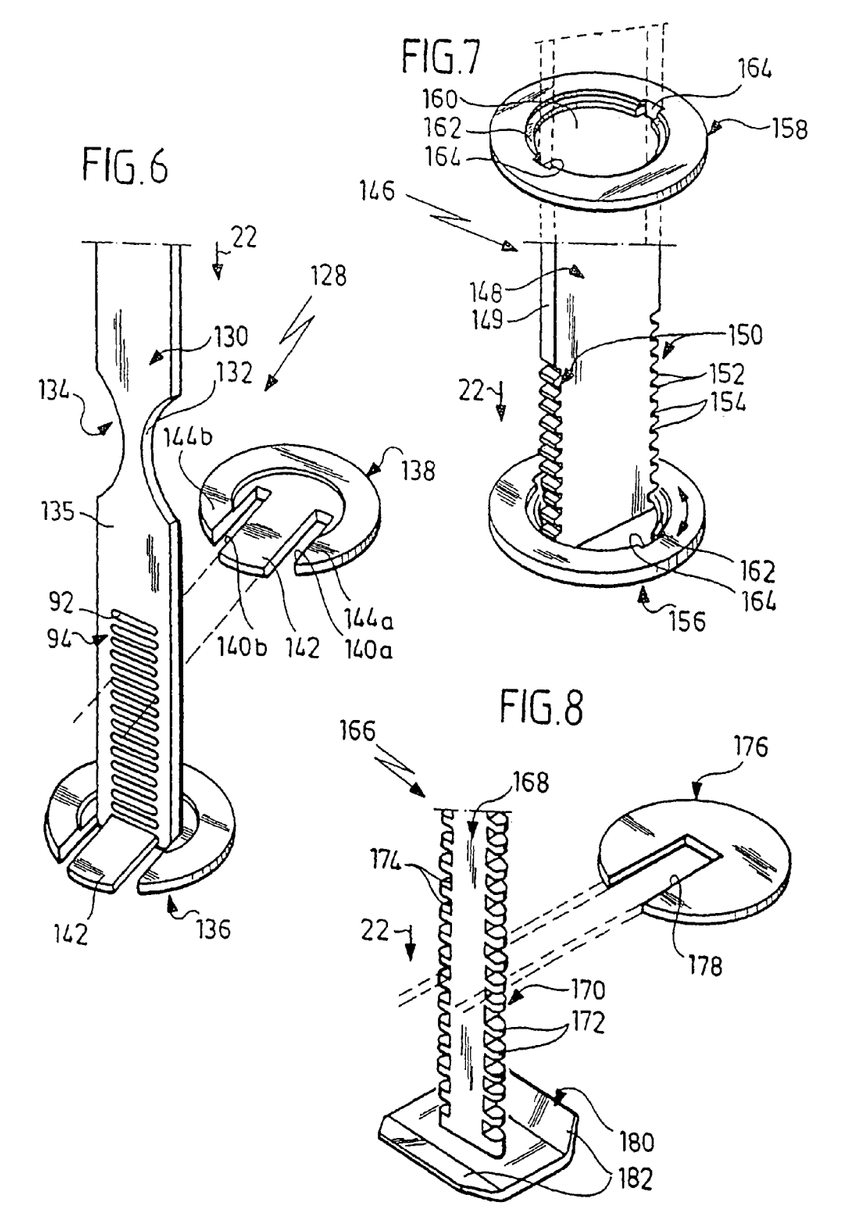
FIG. 6 shows a perspective view of a sixth embodiment of a connecting element according to the invention.
FIG. 7 shows a perspective view of a seventh embodiment of a connecting element according to the invention.
FIG. 8 shows a perspective view of an eighth embodiment of a connecting element according to the invention.

In a sixth embodiment 128 of a connecting element according to the invention, which is shown in FIG. 6, the coupling element 130 is constructed basically as described above. However, the coupling element has as an additional feature a predetermined breaking point 132 which is formed, for example, by the coupling element 130 having a region 134 of reduced cross-section with respect to a longer side 135. The predetermined breaking point serves to bring about breaking of the coupling element 130 when a tensile stress is produced which effects optimum bracing of the bone plates.

In the exemplary embodiment shown in FIG. 6, the first bearing element 136 and the second bearing 138 are again of the same construction. Such a bearing element 136 and 138, respectively, is disc-shaped with slot-like clearances or cut-outs 140a, 140b which run parallel to each other, at a distance from the edge of the disc, towards the inside of such a bearing element 136 and 138, respectively. As a result, a holding tongue 142 for pushing into an opening 92 of the coupling element 130 is formed between the recesses 140a and 140b. Lateral flanks 144a, 144b bordering on the cutouts 140a, 140b provide additional holding of a pushed-in bearing element on the coupling element 130.

In a seventh embodiment 146, which is shown in FIG. 7, a coupling element 148 is provided at each of its opposite lateral surfaces (at the narrow side 149) with engaging strips 150. An engaging strip 150 is designed as a toothed strip with teeth 152 and fixing recesses 154 lying between the teeth.

The first bearing element 156 and the second bearing element 158 are of the same construction with a central feed-through aperture 160, by which, for example, the second bearing element 158 can be pushed onto the coupling element 148. Seated in the feed-through aperture 160 is a circumferential holding tongue 162 which serves for engaging in a fixing recess 154 of an engaging strip 150. The holding tongue 162 is interrupted by radially opposite recesses 164, the width and mutual distance of which are adapted to the corresponding dimensions of the coupling element 148, in order to be able, by way of the recesses 164, to push the second bearing element 158 onto the coupling element 148 and displace it parallel to the longitudinal direction of the coupling element 148.

When the second bearing element 158 has been pushed on, the holding tongue 162 can, by rotation, i.e. by a relative movement between the coupling element 148 and the second bearing element 158 transversely to the clamping direction, be brought into engagement with opposite fixing recesses 154 of the opposite engaging strips 150 and thus the second bearing element 158 can be coupled to the coupling element 148 and, accordingly, frictionally fixed.

In this way, bone plates seated between the first bearing element 156 and the second bearing element 158 (which is connected to the coupling element 148 in the same way as the first bearing element) can then be fixed.

In an eighth embodiment 166, which is shown in FIG. 8, a coupling element 168 has laterally opposite engaging strips 170 with teeth 172 and fixing recesses 174 lying between the teeth 172.

The second bearing element 176 is designed as a disc with a rectangular recess 178 which is oriented parallel to a radial direction. The width of the recess 178 corresponds in this case substantially to a distance between opposite fixing recesses 174 of opposite engaging strips 170. The distance between opposite teeth 172 of an engaging strip 170 corresponds substantially to the thickness of the second bearing element 176.

The second bearing element 176 can be pushed onto the coupling element 168 transversely to the longitudinal direction of the latter.

The first bearing element 180 is, in this exemplary embodiment, integrally formed with the coupling element 168 or positively connected to it and has edge regions 182 which are raised (in the direction of the second bearing element 176 when the latter has been coupled to the coupling element 168) and have a certain elasticity. As a result, on appropriate exertion of a tensile stress after insertion under opposite bone plates, the edge regions 182 can be deformed, then the second bearing element 176 is mounted and, on release of the tensile stress, the force exerted by the elastically deformed edge regions 182 on bone plates lying therebetween brings about an increase in the clamping action between the first bearing element 180 and the second bearing element 176.

Figures 9, 10:
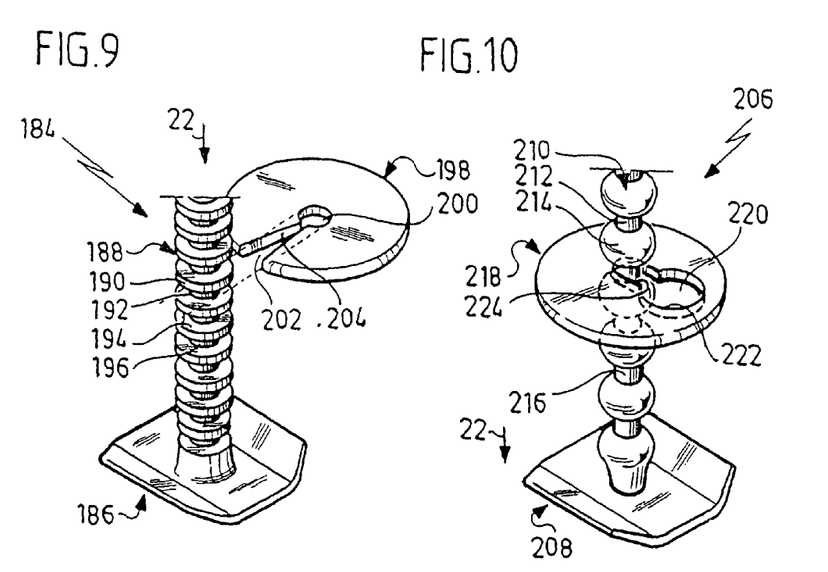
FIG. 9 shows a perspective view of a ninth embodiment of a connecting element according to the invention.
FIG. 10 shows a perspective view of a tenth embodiment of a connecting element according to the invention.

In a ninth embodiment 184, which is shown in FIG. 9, the first bearing element 186 is again integrally connected to a coupling element 188 and is of substantially the same construction as just described for the eighth embodiment.

The coupling element 188 itself has a cylindrical shape with fixing recesses 192 which are formed circumferentially between disc-shaped elements 190 and are thereby bounded by opposite annular surfaces 194 and a cylindrical surface 196 bordering on the opposite annular surfaces 194.

As a result of the radially symmetrical design of the coupling element 188, there is no preferred direction with regard to a deformation transversely to a longitudinal direction. As a result, the connecting element according to the invention, according to the ninth embodiment, can advantageously be employed when a deformation is to be brought about or is expected.

The second bearing element 198 is designed as a disc with a central aperture 200. This central aperture is adapted to the cylindrical surface 196, and is used to hold the second bearing element 198 on the coupling element 188 by virtue of the region around the aperture bearing against the annular surfaces 194. From the edge of the second bearing element to the central aperture 200, the second bearing element 198 has a wedge-shaped cutout 202, by means of which the second bearing element can be pushed onto the coupling element 188 transversely to the longitudinal direction of the latter. In this case, lateral surfaces 204 run towards each other in the direction of the central aperture 200, so that during the pushing-on a force (for opening these lateral surfaces 204) has to be overcome, and when the second bearing element 198 has been pushed on it is held in clamping fashion or at least such that pushing back is impeded.

In a tenth embodiment 206 of a connecting element according to the invention, which is shown in FIG. 10, a first bearing element 208 is integrally connected to a coupling element 210. This coupling element has a cylindrical element 212 which runs in the longitudinal direction and on which spherical elements 214 are arranged spaced apart, fixing recesses 216 being formed between respective adjacent spherical elements 214. The coupling element 210 itself is flexible.

The second bearing element 218 has an opening 220, which comprises a feed-through opening 222, by means of which the second bearing element 218 can be pushed onto the coupling element 210 and moved relative to and in the longitudinal direction of the latter, and furthermore a connected coupling cutout 224, by which the second bearing element 218 can be pushed onto the coupling element 210, transversely to the longitudinal direction of the latter, in order to fix it to the coupling element 210.

As a result of the spherical design of the elements 214, a good clamping action can be achieved even if the first bearing element 208 and the second bearing element 218 are not oriented parallel, for example because the bone plates are not flat, since the spherical shape of the elements 214 enables, at least to a certain extent, pushing on even in a transverse direction deviating from a perpendicular direction.

Figure 11:
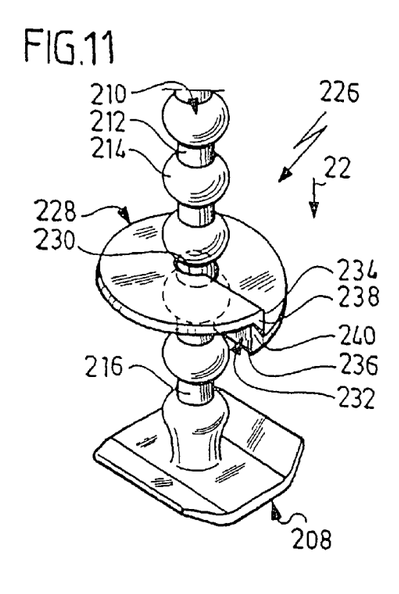
FIG. 11 shows a perspective view of an eleventh embodiment of a connecting element according to the invention.

In an eleventh embodiment 226, which is shown in FIG. 11, the coupling element 210 with the first bearing element 208 seated thereon is of the same design as in the tenth embodiment just described.

A second bearing element 228 is formed by an annular plate which has a central aperture 230 and an introducing recess 232. The introducing recess has opposite lateral surfaces 234 and 236 which are offset in height from each other. Formed on the lateral surface 234 is a tooth 238 pointing in the direction of the lateral surface 236 and on the lateral surface 236 a corresponding tooth 240 pointing in the direction of the lateral surface 234. The two teeth 238 and 240 can interlock after the second bearing element 228 has been pushed onto the coupling element 210, in order to provide improved holding through this additional interlocking.

In particular, provision may be made for the teeth 238 and 240 to be pushed over each other for their interlocking by way of applying forceps.

Figure 12:
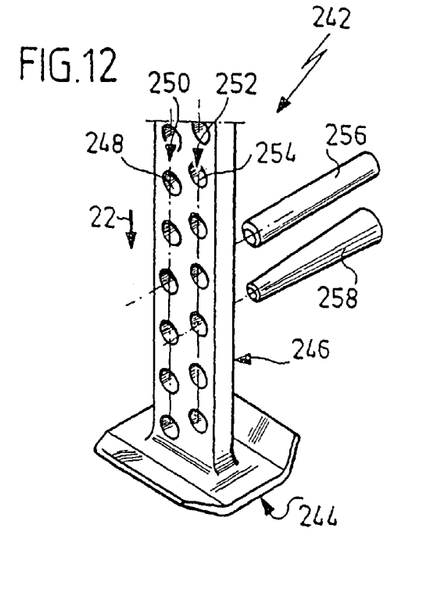
FIG. 12 shows a perspective view of a twelfth embodiment of a connecting element according to the invention.

In a twelfth embodiment 242, which is shown in FIG. 12, a first bearing element 244 is again integrally formed on a coupling element 246, of rectangular cross-section. Arranged in the coupling element 246 is a first row of linearly oriented through-apertures 248 as an engaging strip 250 and, parallel thereto, a further correspondingly designed engaging strip 252, the through-apertures 254 of the engaging strip 252 being offset in height from those of the engaging strip 250; as a result, finer spacing steps for the coupling of a second bearing element 256, 258 are available.

An aperture 248 and 254, respectively, may in this case be of cylindrical design, and a correspondingly adapted second bearing element 256 is then likewise of cylindrical design or has a cylindrical holding tongue.

In a variant of this embodiment, provision may also be made for the apertures 248 and 254, respectively, to taper in one direction, for example be frustoconical. Correspondingly, the second bearing element 258 is then also of frustoconical design. As this second bearing element 258 is pushed into the corresponding apertures 248 and 254, respectively, a wedge action can then be achieved which improves the holding of the second bearing element 258 on the coupling element 246.

Figures 13, 14, 17:
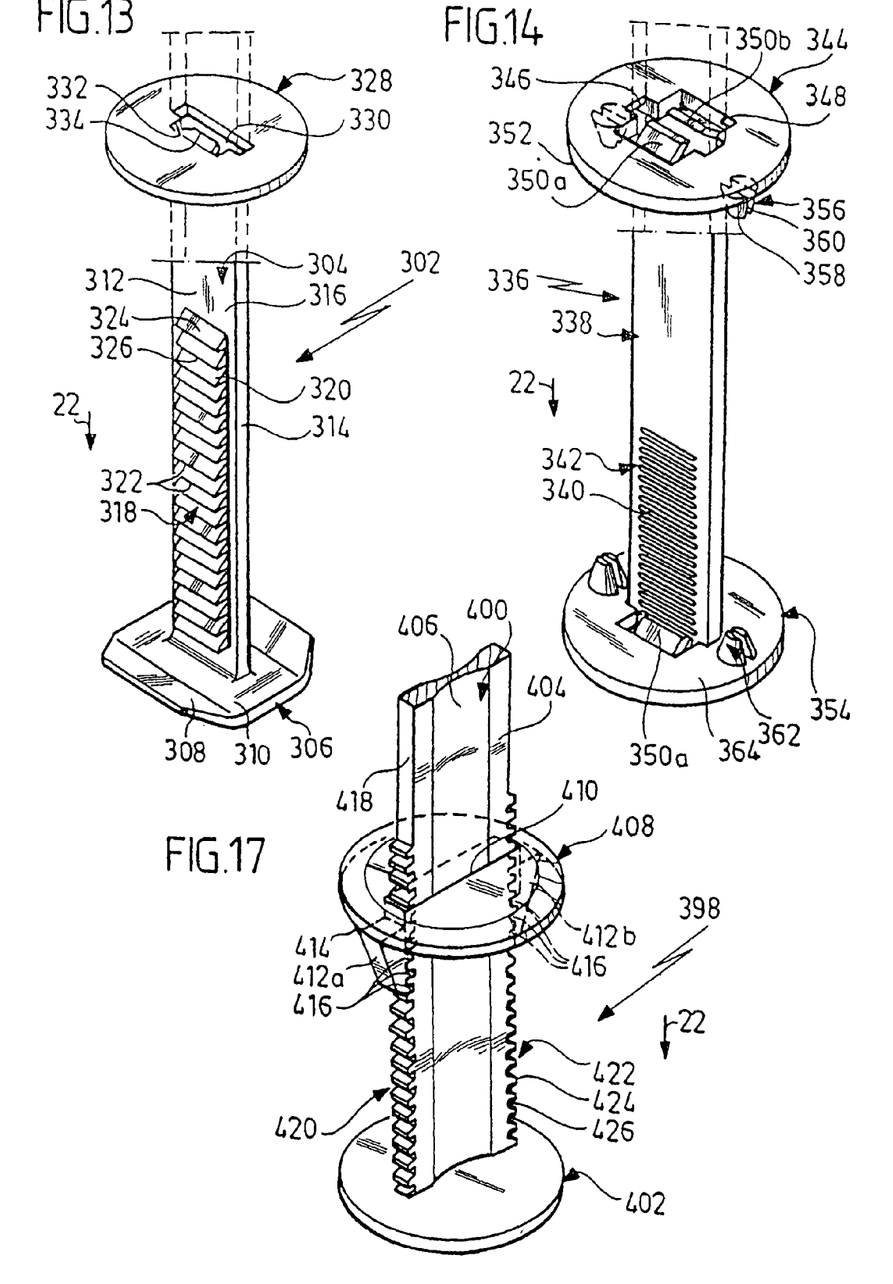
FIG. 13 shows a perspective view of a 13th embodiment of a connecting element according to the invention.
FIG. 14 shows a perspective view of a 14th embodiment of a connecting element according to the invention.
FIG. 16 shows a perspective view of a 16th embodiment of a connecting element according to the invention and FIG. 17 shows a perspective view of a 17th embodiment of a connecting element according to the invention.

In a 13th embodiment of a connecting element according to the invention, which is denoted as a whole by 302 in FIG. 13, a coupling element 304 is integrally connected to a first bearing element 306, which is seated at one end of the coupling element 304. The first bearing element 306 has the shape of a rectangular plate with a raised edge region 308, pointing in the direction of the coupling element 304, on opposite sides of the first bearing element 306. Such an edge region 308 is at an angle from a bearing surface 310 of the first bearing element 306.

The first bearing element 306 is produced from a material with such flexibility that an edge region 308 is deformable under the effect of force in the direction of this edge region, in order to reduce the angle between an edge region 308 and the bearing surface 310.

The coupling element 304 has a rectangular cross-section with a longer side 312 and a narrower side 314, the longer side 312 being substantially parallel to an edge region 308. As a result, the connecting element 302 according to the invention can be inserted into an incision gap 14 by way of the narrower side 314, and the opposite edge regions 308 of the first bearing element 306 abut from below against bone plates to be fixed.

Arranged on an outer surface 316 of the coupling element 304, which surface is formed by the longer side 312 in the longitudinal direction of the coupling element 304, is a toothed strip 318 as an engaging strip. The toothed strip 318 is designed as a latching strip in sawtooth form with teeth 320 of triangular cross-section, having a flank 322 perpendicular to the outer surface 316 and a further flank 324 which, starting from this flank, runs in a direction away from the first bearing element 306 to the outer surface 316. Such a tooth 320 is in this case substantially parallel to the bearing surface 310 of the first bearing element 306.

The toothed strip 318 comprises a plurality of teeth 320 arranged linearly one behind the other and in particular equidistantly. As a result, a fixing recess 326 in the form of a latching recess is formed between the flank 322 of a particular tooth and the flank 324 of a neighboring tooth.

A second bearing element 328 is of disc-shaped design and has a through-aperture 330 of rectangular cross-section adapted to the cross-section of the coupling element 304. By means of this through-aperture 330, the second bearing element 328 can be pushed onto the coupling element 304 and moved relative to the latter in the longitudinal direction of the coupling element 304. The through-aperture 330 is connected to a further opening 332, in which a holding tongue 334 for engaging in a fixing recess 326 is seated. The holding tongue 324 points towards the through-aperture 330 and is in particular of such flexibility that it can be pushed over a flank 324 of a tooth 320 and then after being pushed over the flank latch into a fixing recess 326. This means that, for latching in, the holding tongue 334 executes a movement transversely to the longitudinal direction of the coupling element 304 when the holding tongue returns, from a deformed position by pressing against the sloping flank 324, into its undeformed position in the fixing recess 326. The relative movement between holding tongue 334 and coupling element 304 thus takes place from an unlocked position into a locked position.

The holding tongue 334 is preferably arranged in a plane with the upper and lower surface of the second bearing element 328.

For fixing bone plates lying adjacently between the first bearing element 306 and the second bearing element 328, with the coupling element 304 lying in an incision gap 14, the second bearing element 328 is pushed onto the coupling element 304 and the holding tongue 334 is pushed over the toothed strip 318. As a result of a holding tongue 334 entering into a fixing recess 326, the second bearing element 328 is frictionally fixed to the coupling element 304. As a result, a clamping force can be exerted on the bone plates between the first bearing element 306 and the second bearing element 328 and the bone plates are thereby fixed. Owing to the raised edge regions 308, which deform elastically under tensile stress when bearing against the bone plates and, accordingly, are under bias, this clamping force is increased and hence the fixing is improved.

Provision may be made for the coupling element to have a predetermined breaking point, as has already been described in connection with the sixth embodiment.

In a 14th embodiment 336, as shown in FIG. 14, a coupling element 338 comprises through-openings 340 which have a rectangular cross-section and are arranged parallel at a distance from one another in the form of an engaging strip 342.

A second bearing element 344 is of disc-shaped design with a rectangular through-aperture 346, by means of which the second bearing element 344 can be pushed onto the coupling element 338. Furthermore, an opening 348 is formed in the second bearing element 344 transversely to the through-aperture, on which opening there are oppositely seated holding tongues 350a, 350b which serve for engaging in the openings 340, which are fixing openings. Such a holding tongue 350a, 350b has the form of a spring tongue, which is at an angle from a bearing surface 352 of the second bearing element 344 and faces away from said surface.

On the bearing surface 352, the second bearing element has two holding bodies 356, so that these latter can be positioned, facing the first bearing element 354, in an incision gap 14 between adjacent bone plates. The two holding bodies 356 lie in this case on a connecting line which lies on a diameter of the second bearing element 344. A holding body 356 itself comprises two oppositely arranged holding elements 358 which are of frustoconical design. Between these two holding elements 358 is an intermediate space 360. As a result, the holding elements 358 can be moved towards each other until the intermediate space 360 is bridged and the two holding elements 358 touch.

Holding bodies 356 of such design ensure additional clamping, and the fixing of adjacent bone plates is improved. As a result of the two holding elements 358 of a holding body and the intermediate space 360, the bone plates can in this case still be moved to a certain extent towards each other, enabling corrections with respect to the alignment to be carried out.

In a similar fashion to that already described for the 13th embodiment, the second bearing element 344 is pushed onto the coupling element 338 and the two holding tongues 350a and 350b simultaneously engage in a corresponding opening 340, in order to fix the second bearing element 344 to the coupling element 338.

The first bearing element 354 is basically of the same construction as the second bearing element 344, except that associated holding bodies 362 are arranged on a bearing surface 364 which is the opposite surface to the bearing surface 352 of the second bearing element 344; consequently, the first bearing element 354 and the second bearing element 344 are mirror-symmetrical with each other.

Figure 15:
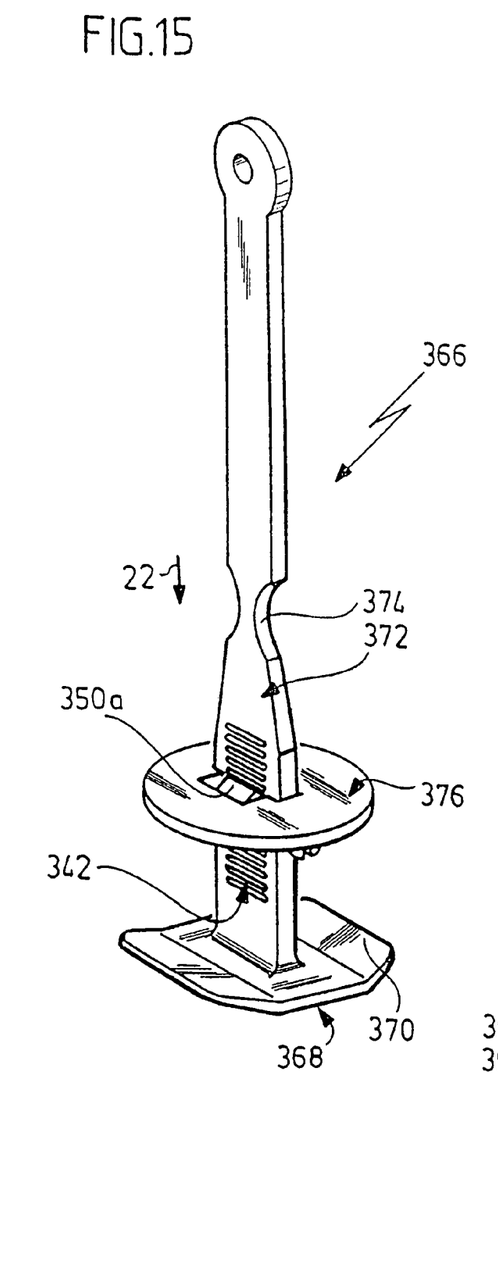
FIG. 15 shows a perspective view of a 15th embodiment of a connecting element according to the invention.

In a 15th embodiment 366, which is shown in FIG. 15, a first bearing element 368 with raised edge regions 370 is integrally connected to a coupling element 372. This coupling element 372 has a predetermined breaking point 374 as described above. A second bearing element 376 is constructed like the second bearing element 344 of the 14th embodiment 336.

Figure 16:
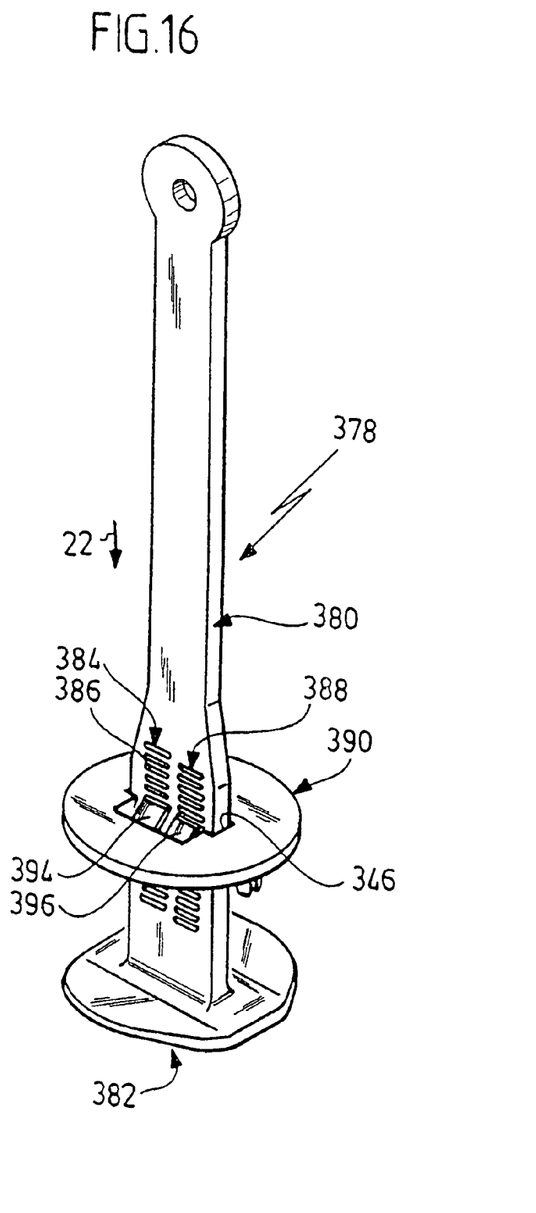

In a variant of the 15th embodiment, which is denoted as a whole by 378 in FIG. 16 (16th embodiment), a coupling element 380, on which a first bearing element 382 is integrally seated, has a first engaging strip 384 with through-openings 386 and a second engaging strip 388 which is arranged parallel thereto but offset in the longitudinal direction of the coupling element 380 in such a way that a through-opening of the second engaging strip 388 is located between adjacent through-apertures of the first engaging strip, with reference to a height in the longitudinal direction of the first coupling element 380. As a result, a finer height adjustment of a second bearing element 390 in relation to the first bearing element 382 can be achieved.

The second bearing element again has, as already described above for the 14th embodiment, a through-aperture 346. However, in an opening 392 transversely thereto there are seated on opposite sides in each case two holding tongues 394 and 396, the holding tongue 394 serving for engaging in the first engaging strip 384 and, accordingly, the second holding tongue 396 serving for engaging in the second engaging strip 388. The second bearing element 390 consequently has a total of four holding tongues which are designed as spring tongues and can engage crosswise on both sides of the engaging strips 384 and 388.

In a 17th embodiment 398, which is shown in FIG. 17, a first disc-shaped bearing element 402 is seated, for example integrally or positively, on a coupling element 400 which has substantially rectangular cross-section, there being centrally formed in the opposite longer sides 404 a recess 406 in the form of an indentation.

A second bearing element 408 is likewise of disc-shaped design with a through-opening 410 which has a rectangular cross-section so that the second bearing element 408 can be pushed onto the coupling element 400. Seated on the second bearing element 408 oppositely on a diameter are holding tongues 412a and 412b which project from a bearing surface 414 of the second bearing element 408. Such a holding tongue 412a and 412b, respectively, is provided, facing the other holding tongue, with a plurality of teeth 416, for example with three teeth arranged spaced apart.

The coupling element 400 has oppositely on opposite lateral surfaces 418 a first engaging strip 420 and a second engaging strip 422, which are each provided with teeth 424, there being formed between adjacent teeth of an engaging strip 420 and 422, respectively, a fixing recess 426 for the engagement of a respective tooth 416 of the second bearing element 408. As a result, the engaging strips 420 and 422 can be positioned in the incision gap 14 so that they do not bear against adjacent bone plates. Provision may be made for the two engaging strips 420 and 422 to be arranged offset in height from each other in such a way that the teeth 424 of the two engaging strips are offset in height relative to each other, in order to achieve a finer height adjustability.

As a result of the plurality of teeth of a holding tongue 412a and 412b, respectively, a plurality of teeth also simultaneously engage in the first engaging strip 420 and the second engaging strip 422, in order thus to obtain secure fixing.

In order to displace the second bearing element 408 on the coupling element 400 or release the fixing, the holding tongues 412a and 412b, respectively, are designed and arranged on the second bearing element 408 with such flexibility that they can be moved away from the engaging strips 420 and 422, respectively, to undo the coupling. A deformation of the second bearing element 408, which takes place during this and which could lead to—undesired—jamming on the coupling element 400, can be taken up here by the recesses 406, so that the displaceability of the second bearing element 408 along the coupling element 400 is not impaired.

The invention claimed is:

1. Surgical connecting element for fixing adjacently arranged bone plates, comprising:
   a first bearing element;
   a second bearing element;
   wherein the second bearing element has at least one holding tongue; and
   a coupling element for coupling the first and second bearing element to each other in such a way that bone plates lying between the first and second bearing element are fixable;
   wherein the coupling element has at least one fixing opening, in which the corresponding holding tongue of the second bearing element is engageable; and
   wherein at least one of the first and second bearing elements has a center panel generally conforming to a first plane and at least one side panel generally conforming to a second plane transverse to the first plane, the first plane and the second plane intersecting at an angle greater than 90 degrees, the at least one side panel and second plane being inclined toward the other of the first and second bearing elements, said at least one side panel being elastically deformable, and said center panel having a flat rectangular three-dimensional shape.

2. Surgical connecting element according to claim 1, wherein the engagement takes place substantially transversely to a clamping direction.

3. Surgical connecting element according to claim 1, wherein the second bearing element and the coupling element are so designed and adapted to each other that, by relative movement between the coupling element and the second bearing element transversely to a clamping direction, the bone plates are fixable between the first and the second bearing element.

4. Surgical connecting element according to claim 1, wherein a fixing position of the first and of the second bearing element is lockable by relative movement between the coupling element and the second bearing element transversely to a clamping direction.

5. Surgical connecting element according to claim 1, wherein at least one of the first and second bearing elements has a holding body which is insertable into an intermediate space between adjacently arranged bone plates.

6. Surgical connecting element according to claim 5, wherein the holding body is designed to be elastic in the direction transverse to a clamping direction.

7. Surgical connecting element according to claim 1, wherein the connecting element is produced from a biocompatible material.

8. Surgical connecting element according to claim 1, wherein the connecting element is fabricated from a resorbable plastic material.

9. Surgical connecting element according to claim 1, wherein the coupling element is provided with a predetermined breaking point.

10. Surgical connecting element according to claim 1, wherein the first bearing element is integrally or positively connected to the coupling element.

11. Surgical connecting element according to claim 1, wherein the second bearing element has at least one through-opening for the coupling element, so that the second bearing element and the coupling element are movable relative to each other substantially parallel to a clamping direction.

12. Surgical connecting element according to claim 1, wherein the second bearing element is connectable to the coupling element by a relative movement of a holding element, seated on the second bearing element, with respect to the coupling element.

13. Surgical connecting element according to claim 1, wherein the coupling element is a rigid body.

14. Surgical connecting element according to claim 1, wherein the coupling element is so dimensioned that in a direction transverse to its longitudinal direction, it has a greater width than in the transverse direction perpendicular thereto.

15. Surgical connecting element according to claim 1, wherein the coupling element has a substantially rectangular cross-section at least in the region which is positionable between adjacent bone plates.

16. Surgical connecting element according to claim 1, wherein the at least one holding tongue of the second bearing element engages in a fixing opening transversely to the clamping direction.

17. Surgical connecting element according to claim 1, wherein the coupling element comprises a plurality of fixing openings which are arranged in the longitudinal direction of the coupling element.

18. Surgical connecting element according to claim 1, comprising a plurality of adjacent fixing openings arranged equidistantly from each other.

19. Surgical connecting element according to claim 1, wherein the coupling element is provided with an engaging strip comprising a plurality of fixing openings.

20. Surgical connecting element according to claim 19, wherein the engaging strip is designed as a latching strip.

21. Surgical connecting element according to claim 19, wherein the coupling element has at least two engaging strips.

22. Surgical connecting element according to claim 21, wherein the at least two engaging strips are arranged offset from one another with respect to a distance of the fixing openings relative to the first bearing element.

23. Surgical connecting element according to claim 19, wherein the engaging strip is of a stepped design.

24. Surgical connecting element according to claim 19, wherein the engaging strip is of a sawtooth design.

25. Surgical connecting element according to claim 19, wherein the engaging strip comprises rectangular openings as fixing openings.

26. Surgical connecting element according to claim 1, wherein a lateral surface of the coupling element is provided with an engaging strip.

27. Surgical connecting element according to claim 1, wherein an engaging strip is arranged on the coupling element between lateral surfaces of the coupling element.

28. Surgical connecting element according to claim 1, wherein the at least one fixing opening has a tapering cross-section.

29. Surgical connecting element according to claim 1, wherein the at least one holding tongue is adapted to enter into the at least one fixing opening by means of which the second bearing element is connectable to the coupling element.

30. Surgical connecting element according to claim 29, wherein the at least one holding tongue comprises a plurality of holding teeth for simultaneous engagement in a plurality of fixing openings.

31. Surgical connecting element according to claim 29, wherein the at least one holding tongue is arranged at an angle to a bearing surface of the second bearing element.

32. Surgical connecting element according to claim 1, wherein the relative movement between the second bearing element and the coupling element for the fixing of the second bearing element to the coupling element proceeds from an unfixed position to a fixing position.

33. Surgical connecting element according to claim 1, wherein the at least one fixing opening comprises a plurality of adjacent fixing openings separated from each other.

34. Surgical connecting element according to claim 33, wherein the adjacent fixing openings are not interconnected.

35. Surgical connecting element according to claim 1, wherein the at least one side panel comprises a pair of side panels on opposing sides of the center panel.

36. Surgical connecting element according to claim 35, wherein the pair of side panels are arranged symmetrically with respect to the coupling element.

37. Surgical connecting element according to claim 35, wherein the coupling element is arranged between the pair of side panels.

38. Surgical connecting element according to claim 1, wherein the at least one side panel has a rim which is elevated with respect to the center panel towards the other of the first and second bearing elements.

39. Surgical connecting element according to claim 1, wherein the at least one side panel comprises a pair of side panels on opposing sides of the center panel, each side panel forming an obtuse angle with the center panel.

40. Surgical connecting element according to claim 1, wherein the at least one side panel comprises a pair of side panels on opposing sides of the center panel, the center panel and side panels each being substantially flat, forming three sides of a trapezoid.

41. A surgical connecting element for fixing adjacently arranged bone plates, comprising:
 a first bearing element;
 a second bearing element;
 wherein the second bearing element has at least one holding tongue; and
 a coupling element for coupling the first and second bearing element to each other in such a way that bone plates lying between the first and second bearing element are fixable;
 wherein the coupling element has at least one fixing opening, in which the corresponding holding tongue of the second bearing element is engageable; and
 wherein the first bearing element has a substantially flat center panel and at least one substantially flat side panel adjacent the center panel, said at least one side panel being elastically deformable to increase a clamping action between the first bearing element and the second bearing element, and said center panel having a flat rectangular three-dimensional shape.

* * * * *